(12) United States Patent  (10) Patent No.: US 8,818,552 B2
Heffron  (45) Date of Patent: Aug. 26, 2014

(54) POINT-OF-CARE MEDICATION DISPENSING

(75) Inventor: David Heffron, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 436 days.

(21) Appl. No.: 11/775,747

(22) Filed: Jul. 10, 2007

(65) Prior Publication Data

US 2009/0014458 A1    Jan. 15, 2009

(51) Int. Cl.
  *G06F 17/00*  (2006.01)
(52) U.S. Cl.
  USPC .......... 700/233; 700/240; 700/237; 700/236
(58) Field of Classification Search
  USPC ................................................ 700/231–244
  See application file for complete search history.

(56) References Cited

U.S. PATENT DOCUMENTS

| | | | | |
|---|---|---|---|---|
| 5,036,462 | A * | 7/1991 | Kaufman et al. | 600/300 |
| 5,084,828 | A * | 1/1992 | Kaufman et al. | 700/242 |
| 5,745,366 | A * | 4/1998 | Higham et al. | 700/242 |
| 5,812,410 | A * | 9/1998 | Lion et al. | 700/231 |
| 6,986,347 | B2 * | 1/2006 | Hickle | 128/200.24 |
| 7,040,504 | B2 * | 5/2006 | Broadfield et al. | 221/98 |
| 7,175,081 | B2 * | 2/2007 | Andreasson et al. | 235/385 |
| 7,260,402 | B1 * | 8/2007 | Ahmed | 455/445 |
| 7,734,371 | B2 * | 6/2010 | Garneau, III | 700/236 |
| 7,996,106 | B2 * | 8/2011 | Ervin | 700/237 |
| 8,032,397 | B2 * | 10/2011 | Lawless | 705/3 |
| 2001/0028308 | A1 | 10/2001 | De La Huerga | |
| 2001/0032035 | A1 * | 10/2001 | Holmes et al. | 700/231 |
| 2003/0052787 | A1 | 3/2003 | Zerhusen et al. | |
| 2003/0105555 | A1 * | 6/2003 | Lunak et al. | 700/237 |
| 2003/0195654 | A1 * | 10/2003 | Spano et al. | 700/237 |
| 2005/0113969 | A1 * | 5/2005 | Spano et al. | 700/237 |
| 2005/0240305 | A1 * | 10/2005 | Bogash et al. | 700/242 |

(Continued)

FOREIGN PATENT DOCUMENTS

EP    1 701 313 A2    9/2006
JP    2005-526540 A    9/2005

(Continued)

OTHER PUBLICATIONS

PCT International Search Report/Written Opinion for International Application No. PCT/US2008/069701 dated Mar. 9, 2009.

*Primary Examiner* — Michael K Collins
(74) *Attorney, Agent, or Firm* — McDermott Will & Emery LLP (57) ABSTRACT

A medication dispenser is provided, comprising a securable container configured to store one or more doses of one or more medications and an access device configured to selectably permit access to the one or more doses. The medication dispenser further comprises an electronic interface configured to acquire user input from a user, and a processor configured to compare the user input to a database, to select, responsive to the comparing, an appropriate dose from the one or more doses, and to permit access through the access device to the appropriate dose. A method for dispensing medication is provided, comprising the steps of locating a medication dispenser at a point-of-care, acquiring user input from a user at the point-of-care, comparing the user input to a database, selecting, responsive to the comparing, an appropriate dose from the one or more doses, and permitting access through the access device to the appropriate dose.

20 Claims, 4 Drawing Sheets

(56) References Cited

U.S. PATENT DOCUMENTS

| | | | |
|---|---|---|---|
| 2006/0155607 A1* | 7/2006 | Bahir | 705/26 |
| 2007/0043469 A1* | 2/2007 | Draper | 700/231 |
| 2007/0185615 A1* | 8/2007 | Bossi et al. | 700/244 |
| 2008/0077440 A1* | 3/2008 | Doron | 705/2 |
| 2008/0228317 A1* | 9/2008 | Ervin | 700/231 |
| 2009/0125324 A1* | 5/2009 | Keravich et al. | 705/2 |

FOREIGN PATENT DOCUMENTS

| | | |
|---|---|---|
| WO | WO-03/058507 A1 | 7/2003 |
| WO | WO-2005/055954 A2 | 6/2005 |
| WO | WO-2006/060291 A2 | 6/2006 |

* cited by examiner

POINT-OF-CARE MEDICATION DISPENSING

CROSS-REFERENCE TO RELATED APPLICATION

Not applicable

STATEMENT REGARDING FEDERALLY SPONSORED RESEARCH OR DEVELOPMENT

Not applicable.

FIELD

Embodiments of the present invention generally relate to medication dispensing and, in particular, relate to point-of-care medication dispensing.

BACKGROUND

Many medications are administered to patients in a hospital setting on an as-needed basis. One such medication, for example, is a patient controlled analgesia (PCA). For this and many other medications, when a patient has a particular symptom, the patient must call for assistance from a nurse and describe the symptom to the nurse. The nurse must then interpret the description provided by the patient, and select an appropriate medication for that symptom and that patient. In certain instances, the nurse will need to consult with a doctor. The nurse must then retrieve the medication, usually from a remote location such as a nurses' station, and return to the patient's room to administer the medication. In such a procedure, there are a number of steps in which the potential for error is high, such as, for example, the nurse misinterpreting the symptom, or selecting the wrong medication or dosage for treatment of the symptom. Moreover, this process introduces significant delay in the treatment of a patient, frequently prolonging the patient's discomfort.

SUMMARY OF THE INVENTION

Embodiments of the present invention address the foregoing problems by providing a medication dispenser at a point of care with which a patient or other authorized user can interact to specify symptoms and from which are dispensed appropriate doses of appropriate medications.

Certain embodiments provide a medication dispenser that comprises a securable container configured to store one or more doses of one or more medications and an access device configured to selectably permit access to the one or more doses of the one or more medications. The medication dispenser further comprises an electronic interface configured to acquire user input from a user and a processor. The processor is configured to perform the steps of comparing the user input to a database, selecting, responsive to the comparing, an appropriate dose from the one or more doses, and permitting access through the access device to the appropriate dose.

Certain embodiments provide a method for dispensing medication that comprises the step of locating a medication dispenser at a point-of-care. The medication dispenser comprises a securable container configured to store one or more doses of one or more medications and an access device configured to selectably permit access to the one or more doses of the one or more medications. The medication dispenser further comprises an electronic interface configured to acquire user input from a user. The method further comprises the steps of acquiring user input from the user at the point-of-care and comparing the user input to a database. The method further comprises the steps of selecting, responsive to the comparing, an appropriate dose from the one or more doses, and permitting access through the access device to the appropriate dose.

Certain embodiments provide a point-of-care medication dispenser that comprises securable means for storing one or more doses of one or more medications, means for selectably permitting access to the one or more doses of the one or more medications, and electronic interface means for acquiring user input from a user. The point-of-care medication dispenser further comprises processing means for performing the steps of comparing the user input to a database, selecting, responsive to the comparing, an appropriate dose from the one or more doses, and permitting access to the appropriate dose through the means for selectably permitting access to the appropriate dose.

It is to be understood that both the foregoing summary of the invention and the following detailed description are exemplary and explanatory and are intended to provide further explanation of the invention as claimed.

BRIEF DESCRIPTION OF THE DRAWINGS

The accompanying drawings, which are included to provide further understanding of the invention and are incorporated in and constitute a part of this specification, illustrate embodiments of the invention and together with the description serve to explain the principles of the invention. In the drawings.

DETAILED DESCRIPTION OF THE INVENTION

In the following detailed description, numerous specific details are set forth to provide a full understanding of the disclosed embodiments. It will be apparent, however, to one ordinarily skilled in the art that the embodiments of the present invention may be practiced without some of these specific details. In other instances, well-known structures and techniques have not been shown in detail to avoid unnecessarily obscuring the disclosure.

Figure 1:
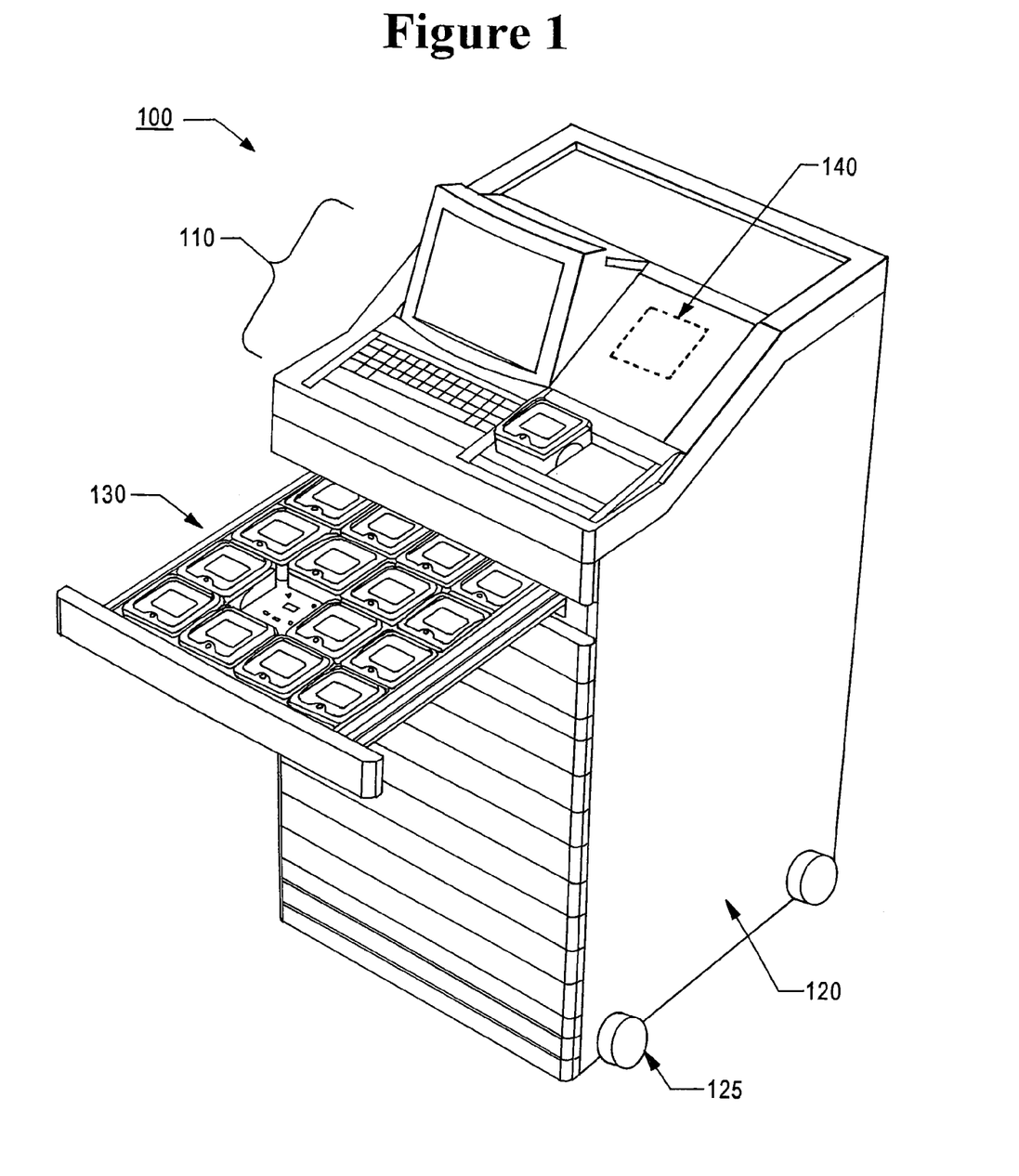
FIG. 1 illustrates a point-of-care medication dispenser in accordance with one embodiment of the present invention.

Referring now to the drawings, FIG. 1 illustrates a point-of-care (POC) medication dispenser 100 in accordance with one embodiment of the present invention. Medication dispenser 100 is located at a point of care to allow a patient or other authorized user to quickly and efficiently procure medications based upon user input regarding, for example, the symptoms experienced by a patient. The medication dispenser 100 allows patients and other authorized users, such as caregivers, to access medications securely stored in the medication dispenser 100 based upon user input regarding symptoms, and upon a database of patient information including, for example, a list of pre-approved medications and doses. When a patient is experiencing symptoms, the patient can input information regarding those symptoms into the electronic interface 110. Based upon this input, a processor 140 within medication dispenser 100 selects an appropriate dose of an appropriate medicine stored within the securable cabinet 120 and permits access to the dose through an access device 130.

By way of example, a patient in a hospital room may experience a headache and require a simple analgesic. Without medication dispenser 100, the patient would likely have to activate a nurse call button, wait for a nurse to respond, describe his symptoms to the nurse, and wait for the nurse to determine the correct medication and dosage, retrieve said medication and return to the patient's room to administer it. Moreover, an overworked nurse might neglect to check the patient's file and discover, for example, his allergy to ibuprofen, a potentially life-threatening mistake. With medication dispenser 100, the patient can, without having to wait for a nurse, provide information regarding his symptoms to the medication dispenser 100, such as by selecting an entry corresponding to "headache" from a touch screen interface. In response to this input, the medication dispenser 100 compares the described symptom to a database correlating symptoms to appropriate medications and cross-referencing information about the patient (e.g., his allergy to ibuprofen, his mass, etc.). Based upon this comparison, the medication dispenser 100 selects an appropriate dose of an appropriate medication (e.g., 200 mg of acetaminophen). This medication, which is stored within secured cabinet 120 in medication dispenser 100 (e.g., in 50 mg dose increments), is then made available to the patient through access device 130. A record of the transaction, including, for example, the user input entered, the medication dispensed, the time of the transaction, etc., is created by medication dispenser 100, and either stored locally or provided to a remote location for review by a health provider.

Alternatively, if the symptoms described by a patient necessitate human intervention (e.g., as when the medication requires administration by a professional), in response to the user input, medication dispenser 100 alerts a nurse or other caregiver at a remote location to come to the patient's room. In a scenario in which the medication requires professional administration (e.g., an injection, enema, etc.), the caregiver would authenticate himself to the medication dispenser 100 with electronic interface 110 and would retrieve the appropriate dose of medication from secured cabinet 120 through access device 130. Similarly, should medication dispenser 100 be unable to determine an appropriate dose of an appropriate medication based upon user input, medication dispenser 100 could alert a caregiver to come to the point of care and select an appropriate medicine from the secured cabinet 120, while retaining a record of the medication dispensed.

In certain embodiments of the present invention, medication dispenser 100 may be configured to require authorization before dispensing medication. For example, while some patients may be capable of limited self-diagnosis and administering some of their own medications, such as analgesia, other patients may not be so capable. Accordingly, an authorized user (e.g., a hospital administrator, a doctor, a nurse, etc.) may configure medication dispenser 100 to require authorization before dispensing a selected medication. In such an instance, a patient will still provide information regarding his symptoms to the medication dispenser 100, in response to which the medication dispenser 100 will compare the described symptom to the and select an appropriate dose of an appropriate medication. Prior to dispensing the selected medication, medication dispenser will generate an alert, which is communicated either locally (e.g., via display, or an audible alarm, or any other notification method) or over a network to an authorized user. The authorized user, such as, for example, a nurse, will then review the selected medication and the patient-described symptoms to ensure that the selected medication is, indeed, appropriate. One the authorized user has provided his or her authorization (either locally, through an input device, or remotely, over a network), the medication dispenser 100 then dispenses the approved medication through access device 130 to a caregiver who then administers the medication.

Accordingly, in certain embodiments of the present invention, a medication dispenser at a point of care provides a number of advantages. For example, dispensing medication at a point of care reduces the time a patient must wait, often in serious discomfort, to obtain a needed dose of medication. Moreover, dispensing medication from a medication dispenser which contains pre-approved doses of pre-approved medications for a particular patient reduces the risk of administering an inappropriate medication to the patient, either due to inappropriate medication selection or accidental misidentification of an appropriately selected medication.

In the present exemplary embodiment of FIG. 1, access device 130 is illustrated as a tray in a drawer within cabinet 120. In certain embodiments, the configuration of access device 130 can be similar to the drawer configuration found in the presently commercially available product known as a MedStation automated medication management system from Cardinal Health, Inc., Dublin, Ohio. A MedStation system can be configured with different kinds of drawers that include drawers with CUBIE receptacles, matrix drawers of different heights, and MiniDrawers™. CUBIE, Matrix and Double Deep Matrix are terms understood by those skilled in the art. CUBIE receptacles, drawers, and related dispensing machines are fully disclosed in U.S. Pat. Nos. 6,116,461 and 6,338,007, which are incorporated herein by reference. There can also be patient-specific CUBIE receptacles that contain multiple medications and supplies for a single patient.

In certain other embodiments, access device 130 can be much simplified, and may include only a single drawer, for example, and only a touch screen interface. The access device 130 as illustrated in FIG. 1 is therefore only one example of the many access devices that may be included in a medication dispenser in accordance with various embodiments of the present invention.

In certain embodiments of the present invention, a medication dispenser may contain multiple access devices or a single access device for permitting access to any of the medications stored within a secured cabinet. In certain embodiments of the present invention, an access device may not be a drawer. For example, in a manner similar to that employed by vending machines, a medication dispenser may contain rows of medication doses stored horizontally above an access tray, such that the medication dispenser can actuate a mechanism to push appropriate doses of medication over the access tray whereupon gravity will bring the doses within reach of the patient or caregiver. The foregoing embodiments are merely exemplary of the many access devices suitable for use in a medication dispenser configured in accordance with embodiments of the present invention. Rather, the present invention has application to medication dispensers with any manner of access device, including doors, drawers, trays, cups, plungers, helices, etc., any of which may translate, rotate, open, actuate, etc.

The terms "point of care" and "point-of-care," as used herein, are used to refer to a placement of a medication dispenser in close proximity to a patient or patients. For example, in accordance with various aspects of the present invention, a point of care may be a room, such as a hospital room, a bedroom in a home in which a patient is treated, an emergency room servicing multiple patients, and the like.

According to one aspect of the present invention, POC medication dispenser 100 is portable. As can be seen with reference to FIG. 1, medication dispenser 100 is provided with ground-engaging wheels 125 (an embodiment with four wheels is shown), and a handle for use in transporting medication dispenser 100. In certain embodiments, other methods of movement may be used. In certain embodiments, depending on the location and type of electronic interface 110, the cabinet 120 can also have a top work surface which can vary in size and shape depending on the type of electronic interface 110 used.

In accordance with various aspects of the present invention, the electronic interface 110 can be located on the cabinet 120 removably or permanently. In certain embodiments, portions of the electronic interface 110 can be attached to the cabinet 120 via an arm, such as an articulated arm, to ease user interface with the input device 114.

In certain embodiments, the medication dispenser 100 can include an illumination light for illuminating the drawers. In this way, an opened drawer's contents are illuminated obliquely. This illumination light may be positioned in the cabinet handle or attached to the underside of the handle. The illumination light is turned on when a drawer is opened. The drawers may also incorporate translucent bins and gentle illumination from below to silhouette the drawer contents.

In accordance with one aspect of the present invention, the cabinet is secured such as, for example, by an electronic solenoid. In the event that there is a loss of power to medication dispenser 100, and/or some electrical computer malfunction prevents normal access to the access devices 130, the cabinet 120 can be equipped with a manual release mechanism for use in unlocking the drawers. In certain embodiments, various other means for securing cabinet 120 may be used, such as, for example, mechanically actuated pins, arms, flanges and the like, electromagnets, etc.

Figure 2:
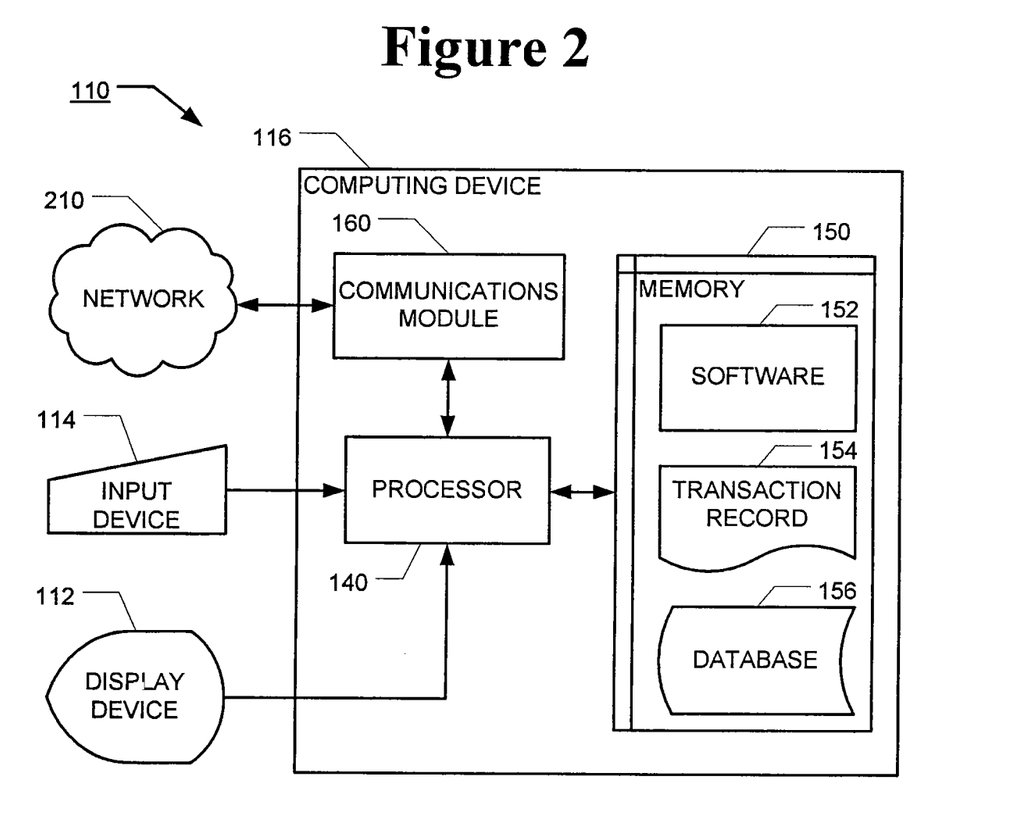
FIG. 2 is a block diagram illustrating an electronic interface of a medication dispenser in accordance with one embodiment of the present invention.

FIG. 2 is a block diagram of the electronic interface 110 of medication dispenser 100 in accordance with one embodiment of the present invention. The electronic interface 110 comprises a computing device 116, a display device 112 and an input device 114.

In accordance with the present exemplary embodiment of the present invention, the display device 112 is a flat panel display. In certain embodiments, the display device 112 may alternately be a cathode ray tube (CRT) display, vacuum fluorescent display (VFD), light emitting diode (LED) display, plasma display panel (PDP), liquid crystal display (LCD), organic light emitting diode (OLED), or surface-conduction electron-emitter display (SED).

Figure 3:
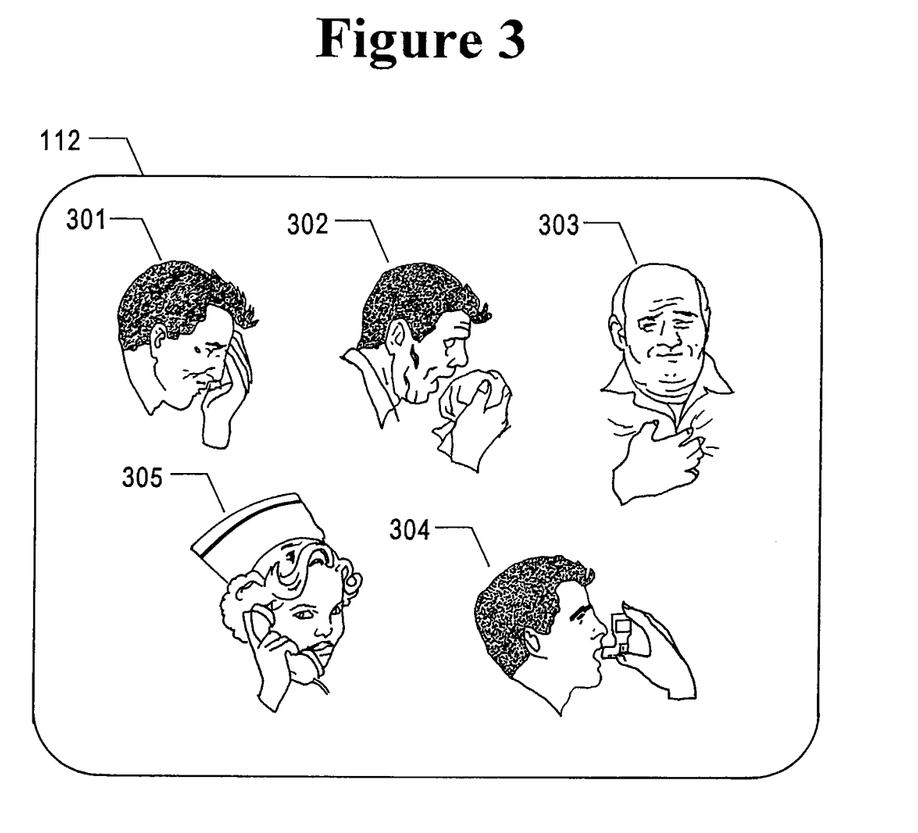
FIG. 3 illustrates an input device for a point-of-care medication dispenser in accordance with one embodiment of the present invention.

In certain embodiments, input device 114 is a touch-screen input with simplified icons suitable for use by a patient. For example, a simplified touch screen input device 114 is illustrated in FIG. 3, in accordance with one embodiment of the present invention. A variety of pictographic icons (301-305) illustrate various ailments in a manner easily understood by patients. For example, a patient experiencing a headache could click on pictographic icon 301, indicating the need for a simple analgesia, while a patient experiencing aggravated allergies could click on pictographic icon 302, indicating the need for an antihistamine. Pictographic icons 303 and 304 might be selected by a patient experiencing heart pain or respiratory problems, respectively. In the event the patient needed assistance from a caregiver, pictographic icon 305 could be selected to alert a nurse to come and select an appropriate medication from the medication dispenser, using an alternative input method (e.g., a keyboard, keypad, etc.). Such simple pictographic icons allow a patient with difficulty reading text, such as, for example, a patient with poor eyesight, or one lacking literacy in the language in which the medication dispenser is configured to operate, to interact effectively with the medication dispenser. In certain embodiments, medication dispenser 100 may be configured to interact with users in more than one language, to effectively serve patients and caregivers who speak and/or read different languages.

In certain embodiments, input device 114 may be a keyboard. In certain other embodiments, the input device 114 can be a keypad integral with the cabinet, a mouse, or a microphone. For example, in embodiments without a physical keyboard, the input device 114 can be a virtual keyboard. The virtual keyboard automatically appears on the display device 112 when the system detects a type-in field. The virtual keyboard is a feature that hospital staffs appreciate even more than the physical keyboards because it minimizes the number of objects in the room and also decreases the risk of infection and contamination. In still other embodiments of the present invention, an input device may include any combination of eye movement tracking devices, motion sensing devices, buttons, knobs, levers, switches, dials, handles, latches, triggers, cranks, wheels, joysticks, mice, track pads, trackballs, or any other input device capable of receiving user input.

According to one embodiment of the present invention, the computing device 116 comprises a processor 140, memory 150, and a communications module 160. The processor 140, for example, a central processing unit (CPU), executes software from the computing device's memory 150. The communications module 160 provides networking capability in order to connect to a network 210 which is described in further detail below. Networking capability is achieved via a communication layer that enables data transmissions. In various embodiments of the present invention, networking can be achieved by the use or the installation of data cables from the medication dispenser 100 to a central network device for the network 210, such as a router or switch, or by using a wireless connection. An alternate technology uses existing phone cabling of the facility to transport data, thus avoiding the cost and deadlines associated with the installation of new cabling.

Stored in the memory 150 is software 152 for dispensing medication, a transaction record 154, and a database 156. The memory 150 can include volatile and/or non-volatile sections. The electronic interface 110 uses software 152 to control access to items stored in the cabinet 120.

For example, in one embodiment of the present invention, software 152 includes code for interacting with a user of medication dispenser 100, such that the user can provide user input indicating his or her symptoms by, for example, selecting from a list of symptoms displayed on a screen. Software 152 further includes code for comparing the user input to database 156 to determine an appropriate dose of an appropriate medication. For example, database 156 may include a list of pre-approved doses of pre-approved medications for a given patient, with symptoms corresponding to each medication. Thus, software 152 compares the symptoms input by the user to this and selects a match, if found. In response to finding a match, software 152 then permits access through the access device of the medication dispenser 100 to the appropriate dose selected.

In the event a match is not found in the comparison step, software 152 can further include code for alerting a caregiver, such as, for example, a nurse or nurse practitioner, over network 210. For example, a computer at a remote location, such as a nursing station, may also be connected to network 210, such that software 152, finding no match in database 156 for the symptoms provided by the user, can send an alert over network 210 to the remote computer with information about the patient and the indicated symptom, either so that an authorized caregiver at the remote location can remotely indicate which of the medications stored in cabinet 120 is appropriate given the input (and thereby direct software 152 to provide access to the medication through access device 130), or so that a caregiver can respond by coming to the point of care to administer an appropriate medication or obtain further information from the user of medication dispenser 100. In one aspect of the present invention, even if a match is found in the comparison step, software 152 may still provide an alert to a remote caregiver, such as, for example, a nurse at a nurses' station, in which the described symptom and selected medication and dose are provided for the nurse's review and authorization.

In certain embodiments of the present invention, software 152 may also provide a mechanism for allowing a remote caregiver to override a selection made by software 152. In such an embodiment, a remote caregiver may be alerted over network 210 to the selection made by software 152. Prior to dispensing the selected dose, the software 152 may allow a predetermined time period to elapse, in which the remote caregiver can instruct medication dispenser 100 to refrain from dispensing the selected medication, and to dispense a different medication. Alternatively, instead of a predetermined time period, some selected medications may require an affirmative approval from a caregiver. In such an instance, software 152 may alert a remoter caregiver to the selection, and wait for approval to be provided before dispensing the selected medication.

Software 152 further includes code for maintaining a record of the transactions which occur at medication dispenser 100. For example, each time a user provides user input, the user input is logged in the transaction record 154. Each time a medication is selected and/or dispensed, the selection and/or dispensing of the medication is likewise logged in the transaction record 154. In this manner, caregivers can access a detailed log including a patient's symptoms, medication doses, etc. This log may be accessed locally, when a caregiver or other authorized user interacts with the electronic interface 110, or remotely, when a caregiver or other authorized user interacts with medication dispenser 100 over network 210. Accordingly, software 152 also includes code for allowing access to the transaction record by authorized users, who may authenticate with a password, keycard, or other authentication method known to those of skill in the art.

In addition to a list of pre-approved doses of pre-approved medications, database 156 also includes information about the stocking levels of medications available in cabinet 120, in accordance with one aspect of the present invention. For example, when a dose of a medication is dispensed, software 152 may update database 156 to reduce the available doses of the medication dispensed by the amount dispensed. In this manner, inventory control is made more convenient. Software 152 may include code for allowing authorized users to locally (using electronic interface 110) or remotely (over network 210) check the stock level of a given medication, and may further include code for providing alerts when a medication stock level reaches a predetermined level.

According to one aspect, software 152 also includes code for allowing authorized users to modify database 156. For example, a caregiver such as, for example, an attending doctor or a pharmacist may wish to add or remove a medication from the list of pre-approved medications for a patient associated with medication dispenser 100. Accordingly, software 152 provides an authentication method for allowing the caregiver to access database 156 and to edit it using electronic interface 110.

In one embodiment of the present invention, database 156 is stored not in memory 150, but remotely from medication dispenser 100, and is accessed by software 152 over network 210. In this manner, a centralized database may be kept in, for example, a hospital server, and maintained by a central authority, while multiple individual medication dispensers can access the database to get up-to-date information about authorized doses of authorized medications for associated patients.

In embodiments where tracking of items is included, software 152 allows the needed item to be retrieved and recorded on-screen. This mode of interaction works best for caregivers with a clear mental picture of where items are in the cabinet 120, or who can quickly recognize an item on sight. This mode also allows items to be accessed and recorded while the software 152 is in mid-operation on another task. In another embodiment, the display device 112 provides a screen interface for each drawer in the cabinet 120. This interface may illustrate any and all the items and their locations in drawer sections. This may be shown graphically with pictures or a list of items and their locations. This may help the caregiver to intuitively direct their attention to relevant items. If the caregiver takes nothing from the drawer, the on screen menu for that drawer will persist (even if the drawer has been shut again) until the caregiver presses the "none taken" button or goes to the next screen if another drawer is opened. If the caregiver has taken item(s) and has recorded what the caregiver has taken on the touch screen, the menu will disappear when the caregiver shuts the drawer. In another embodiment, an "out of stock" button can be provided beside each item button to inform restockers about items that need more urgent attention—for example, a nurse needed a particular item but the item was not there. In yet another embodiment, a "dispatch" button could be provided to get a restocker to come to the room immediately with a refill.

In certain embodiments, the memory 150 further includes a Bedside Information Gateway™ (BIG). BIG is an application-independent system that allows easy and efficient access to mission-critical applications directly from the medication dispenser 100. It makes it possible for medical staff to leverage applications throughout the facility regardless of the technology (Web or Windows) used for these applications. BIG makes it possible for physicians and nurses to access quickly and easily a wide variety of medical applications and information, therefore shortening the time it takes the caregiver to make rounds. Whether used to consult a patient file, access laboratory/radiology results or prescriptive applications, the medication dispenser 100 simply acts as a window on the applications inside the hospital mainframe, such as by using the network 210.

Figure 4:
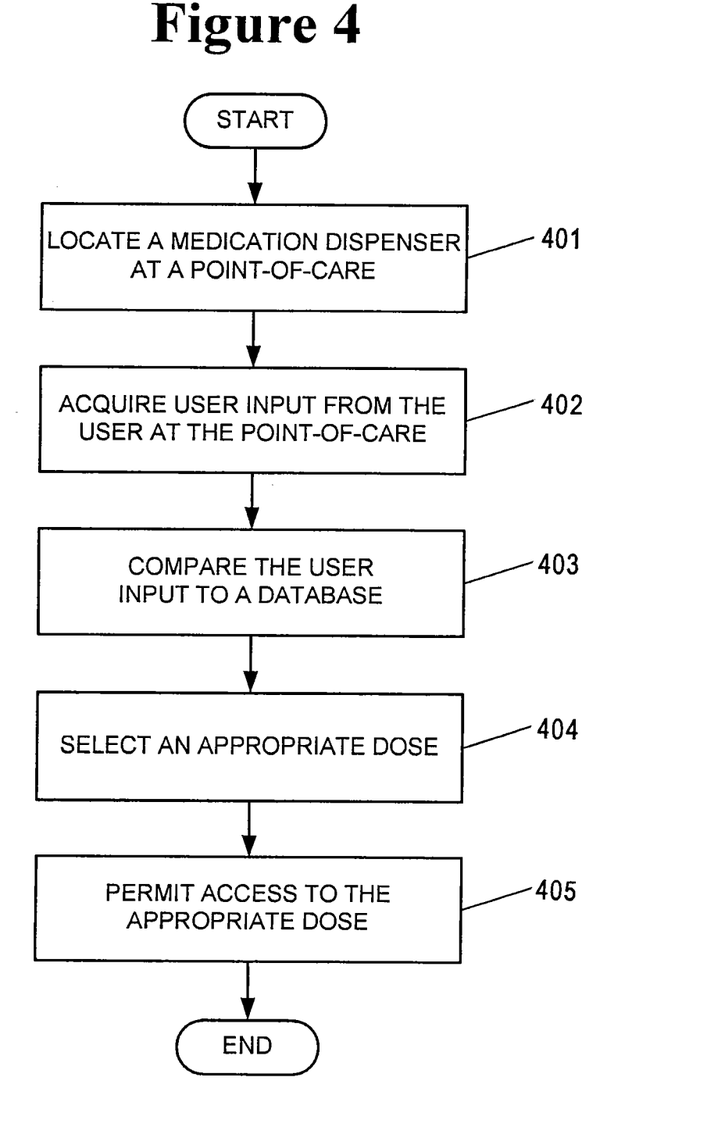
FIG. 4 is a flow chart illustrating a method for dispensing medication in accordance with one embodiment of the present invention.

FIG. 4 is a flow chart illustrating a method for dispensing medication in accordance with certain embodiments of the present invention. The process begins with step 401, in which a medication dispenser is located at a point-of-care. The medication dispenser includes a securable container configured to store one or more doses of one or more medications, an access device configured to selectably permit access to the one or more doses of the one or more medications, and an electronic interface configured to acquire user input from a user. In step 402, user input is acquired from a user at the point-of-care. The user may be a patient, a caregiver, or any other authorized personnel. In step 403, the user input is compared to a database containing information about pre-approved doses of pre-approved medications contained within the securable container. In step 404, an appropriate dose corresponding to the user input is selected, responsive to the comparison, from the one or more doses in the securable container. In step 405, access to the selected appropriate dose is permitted through the access device in the medication dispenser, such as by, for example, an opening door, drawer, tray or cup.

While the present invention has been particularly described with reference to the various figures and embodiments, it should be understood that these are for illustration purposes only and should not be taken as limiting the scope of the invention. There may be many other ways to implement the invention. Many changes and modifications may be made to the invention, by one having ordinary skill in the art, without departing from the spirit and scope of the invention.

What is claimed is:

1. A medication dispenser, comprising:
   a securable container configured to store one or more doses of one or more medications;
   an access device configured to selectably permit access to the one or more doses of the one or more medications;
   an electronic interface configured to acquire user input from a user comprising information about at least one patient symptom of a patient; and
   a processor configured to perform the steps of:
      comparing the information about the at least one patient symptom to a database,
      determining, responsive to the comparison of the information about the at least one patient symptom to the database, a specific medication from a plurality of different medications, and for the determined specific medication, determining an appropriate dose, from a range of the one or more doses, of the determined specific medication corresponding to the at least one patient symptom,
      selecting the appropriate dose of the determined specific medication, and
      permitting access through the access device to the appropriate dose.

2. The medication dispenser of claim 1, wherein at least one of the one or more medications is a non-prescription medication.

3. The medication dispenser of claim 1, wherein the electronic interface comprises a touch screen.

4. The medication dispenser of claim 1, wherein the user is the patient.

5. The medication dispenser of claim 1, wherein the database comprises information about approved medications for the patient.

6. The medication dispenser of claim 1, wherein the database comprises information correlating the at least one patient symptom to the one or more medications.

7. The medication dispenser of claim 1, wherein the permitting access comprises providing an alert to a health care provider and permitting access through the access device to the health care provider.

8. The medication dispenser of claim 1, wherein the permitting access comprises permitting access through the access device to the user.

9. The medication dispenser of claim 1, wherein the processor is further configured to keep a record of dispensed medications.

10. The medication dispenser of claim 1, wherein the determining the medication from a plurality of medications and the appropriate dose of the medication corresponding to the at least one patient symptom is further responsive to at least one of the patient's allergy or the patient's weight.

11. A method for dispensing medication, the method comprising the steps of:
    locating a medication dispenser at a point-of-care, the medication dispenser comprising:
       a securable container configured to store one or more doses of one or more medications;
       an access device configured to selectably permit access to the one or more doses of the one or more medications; and
       an electronic interface configured to acquire user input from a user comprising information about at least one patient symptom;
    acquiring user input from the user at the point-of-care;
    comparing the information about the at least one patient symptom to a database,
    determining, responsive to the comparison of the information about the at least one patient symptom to the database, a specific medication from a plurality of different medications, and for the determined specific medication, determining an appropriate dose, from a range of the one or more doses, of the determined specific medication corresponding to the at least one patient symptom,
    selecting the appropriate dose of the determined specific medication, and
    permitting access through the access device to the appropriate dose,
    wherein the medication dispenser further comprises a processor, and wherein the steps of comparing, determining, and selecting are performed by the processor.

12. The method of claim 11, wherein at least one of the one or more medications is a non-prescription medication.

13. The method of claim 11, wherein the electronic interface comprises a touch screen.

14. The method of claim 11, wherein the user is the patient.

15. The method of claim 11, wherein the database comprises information about approved medications for the patient.

16. The method of claim 11, wherein the database comprises information correlating the at least one patient symptom to the one or more medications.

17. The method of claim 11, wherein the permitting access comprises providing an alert to a health care provider and permitting access through the access device to the health care provider.

18. The method of claim 11, wherein the permitting access comprises permitting access through the access device to the user.

19. The method of claim 11, further comprising the step of:
    keeping a record of dispensed medications.

20. A point-of-care medication dispenser, comprising:
    securable means for storing one or more doses of one or more medications;
    means for selectably permitting access to the one or more doses of the one or more medications;
    electronic interface means for acquiring user input from a user comprising information about at least one patient symptom; and
    processing means for performing the steps of:
       comparing the information about the at least one patient symptom to a database,
       determining, responsive to the comparison of the information about the at least one patient symptom to the database, a specific medication from a plurality of different medications, and for the determined specific medication, determining an appropriate dose, from a range of the one or more doses, of the determined specific medication corresponding to the at least one patient symptom, selecting the appropriate dose of the determined specific medication, and permitting access to the appropriate dose through the means for selectably permitting access to the appropriate dose.

* * * * *